US006177103B1

(12) United States Patent
Pace et al.

(10) Patent No.: US 6,177,103 B1
(45) Date of Patent: Jan. 23, 2001

(54) PROCESSES TO GENERATE SUBMICRON PARTICLES OF WATER-INSOLUBLE COMPOUNDS

(75) Inventors: Gary W. Pace, Raleigh, NC (US); Michael G. Vachon; Awadhesh K. Mishra, both of Quebec (CA); Inge B. Henrikson, Stavanger (NO); Val Krukonis, Lexington, MA (US)

(73) Assignee: RTP Pharma, Inc., Durham, NC (US)

( * ) Notice: Under 35 U.S.C. 154(b), the term of this patent shall be extended for 0 days.

(21) Appl. No.: 09/335,735

(22) Filed: Jun. 18, 1999

Related U.S. Application Data

(60) Provisional application No. 60/089,852, filed on Jun. 19, 1998.

(51) Int. Cl.⁷ ........................................... A61K 9/14
(52) U.S. Cl. ................................................ 424/489
(58) Field of Search .............................. 424/489

(56) References Cited

U.S. PATENT DOCUMENTS 3,998,753   12/1976  Antoshkiw et al. ............. 252/312
5,922,355  * 7/1999  Parikh et al. .................... 424/489

FOREIGN PATENT DOCUMENTS 0 744 992 B1    12/1996   (EP).
WO 95/21688     8/1995    (WO).
WO 97/14407  *  4/1997    (WO).
WO 98/07414     2/1998    (WO).
WO 99/52504    10/1999    (WO).

OTHER PUBLICATIONS

G. Donsi et al. Pharm. Acta Helv, 1991, pp. 170–173, "Possibility of Application to Pharmaceutical Field".

* cited by examiner

*Primary Examiner*—Shelley A. Dodson
*Assistant Examiner*—Konata M. George
(74) *Attorney, Agent, or Firm*—Nixon & Vanderhye

(57) ABSTRACT

Submicron particles of water-insoluble compounds, particularly drugs, are prepared by simultaneously stabilizing microparticulate suspensions of same with surface modifier molecules by rapid expansion into an aqueous medium from a compressed solution of the compound and surface modifiers in a liquefied gas and optionally homogenizing the aqueous suspension thus formed with a high pressure homogenizer.

15 Claims, 2 Drawing Sheets

VOLUME-WEIGHTED NICOMP DISTRIBUTION ANALYSIS
(SOLID PARTICLES)

NICOMP SUMMARY:
Peak Number 1 : Mean Diameter = 22.7 nm   Volume: 100.00 %

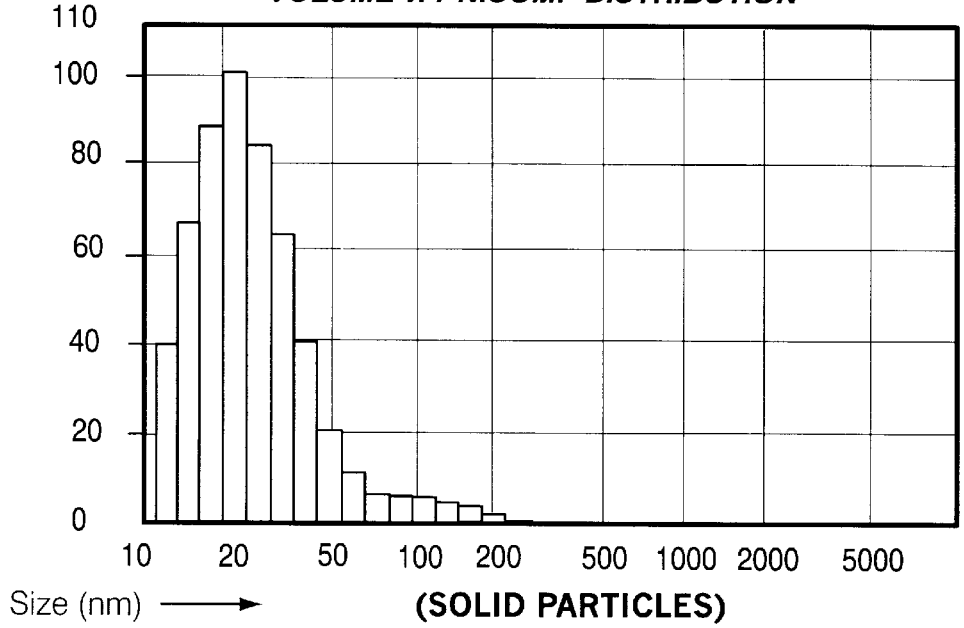

Mean Diameter = 30.1 nm     Pit error = 3.897     Residual = 2.015

NICOMP SCALE PARAMETERS:
Min. Diam. = 10.0 nm          Plot Size = 36
Smoothing = 4                 Plot Range = 1000

| | | | |
|---|---|---|---|
| Run Time | = 0 Hr 7 Min 26 Sec | Wavelength | = 632.8 nm |
| Count Rate | = 301   Khz | Temperature | = 21 deg C |
| Channel #1 | = 267.8  K | Viscosity | = 0.933 cp |
| Channel Width | = 11.0    uSec | Index of Ref. | = 1.333 |

GAUSSIAN SUMMARY:
| | | | |
|---|---|---|---|
| Mean Diameter | = 37.7 nm | Chi Squared | = 36.603 |
| Stnd. Deviation | = 22.1 nm (58.6%) | Baseline Adj. | = 0.016% |
| Coeff. of Var'n | = 0.586 | Mean Diff. Coeff. | = 1.24E-07 cm$^2$/s |

Fig. 1

VOLUME-WEIGHTED GAUSSIAN ANALYSIS
(SOLID PARTICLES)

GAUSSIAN SUMMARY:

| | | | |
|---|---|---|---|
| Mean Diameter | = 86.0 nm | Chi Squared | = 0.218 |
| Stnd. Deviation | = 24.9 nm (29.0%) | Baseline Adj. | = 0.012% |
| Coeff. of Var'n | = 0.290 | Mean Diff. Coeff. | = 5.37E-08 $cm^2$/s |

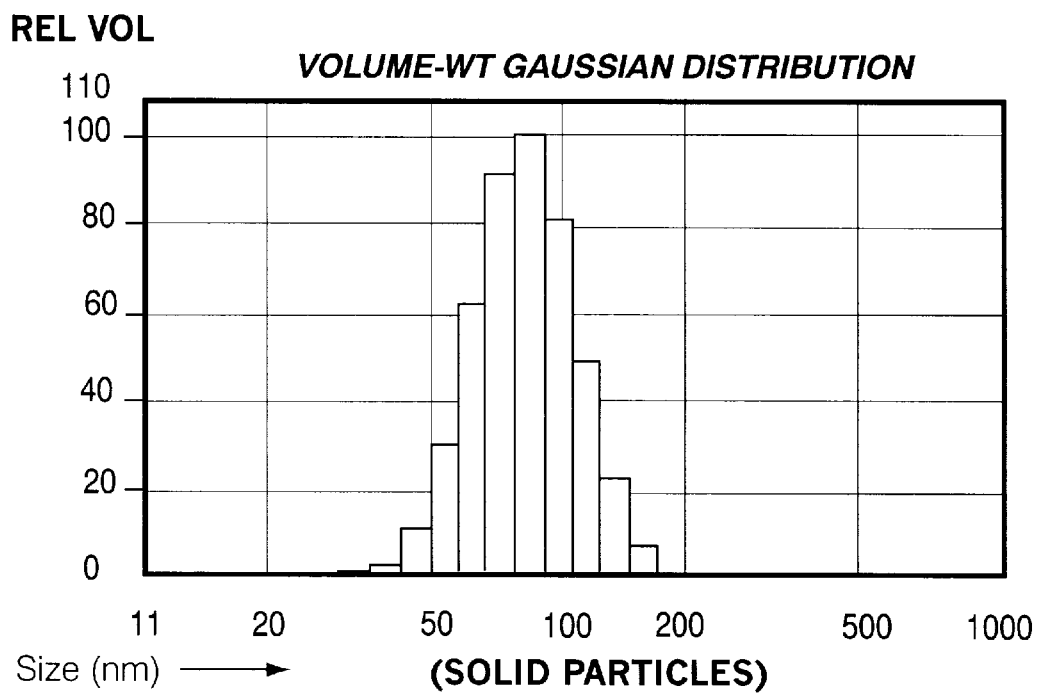

Cumulative Results:
25 % of distribution < 62.68 nm
50 % of distribution < 76.22 nm
75 % of distribution < 93.05 nm
99 % of distribution < 151.39 nm

| | | | | |
|---|---|---|---|---|
| Run Time | = 0 Hr 7 Min 12 Sec | | Wavelength | = 632.8 nm |
| Count Rate | = 324 | Khz | Temperature | = 21 deg C |
| Channel #1 | = 310.1 | K | Viscosity | = 0.933 cp |
| Channel Width | = 12.0 | uSec | Index of Ref. | = 1.333 |

Fig. 2

PROCESSES TO GENERATE SUBMICRON PARTICLES OF WATER-INSOLUBLE COMPOUNDS

This application claims benefit to provisional 60/089,852 filed Jun. 19, 1998.

This invention provides processes for producing micrometer and sub-micrometer sized particulate preparations of biologically useful compounds that are water-insoluble or poorly water-soluble, particularly water-insoluble pharmaceutical agents.

BACKGROUND AND SUMMARY OF INVENTION

A major problem in formulating biologically active compounds is their poor solubility or insolubility in water. For instance, over one third of the drugs listed in the United States Pharmacopoeia are either water-insoluble or poorly water-soluble. Oral formulations of water-insoluble drugs or compounds with biological uses frequently show poor and erratic bioavailability. In addition, drug insolubility is one of the most recalcitrant problems facing medicinal chemists and pharmaceutical scientists developing new drugs. Water-insolubility problems delay or completely block the development of many new drugs and other biologically useful compounds, or prevent the much-needed reformulation of certain currently marketed drugs. Although the water-insoluble compounds may be formulated by solubilization in organic solvents or aqueous-surfactant solutions, in many cases such solubilization may not be a preferred method of delivery of the water-insoluble agent for their intended biological use. For instance, many currently available injectable formulations of water-insoluble drugs carry important adverse warnings on their labels that originate from detergents and other agents used for their solubilization.

An alternative approach for the formulation of water-insoluble biologically active compounds is surface-stabilized particulate preparations. Small particle size formulation of drugs are often needed in order to maximize surface area, bioavailability and, dissolution requirements. Pace et al. ("Novel Injectable Formulations of Insoluble Drugs" in Pharmaceutical Technology, March 1999) have reviewed the usefulness of the microparticulate preparations of water-insoluble or poorly soluble injectable drugs.

In U.S. Pat. Nos. 5,091,187 and 5,091,188 to Haynes describe the use of phospholipids as surface stabilizers to produce aqueous suspension of submicron sized particles of the water-insoluble drugs. These suspensions are believed to be the first applications of the surface modified microparticulate aqueous suspension containing particles made up of a core of pure drug substances and stabilized with natural or synthetic bipolar lipids including phospholipids and cholesterol. Subsequently, similar delivery systems exploiting these principles have been described (G. G. Liversidge et al., U.S. Pat. No. 5,145,684; K. J. Illig et al. U.S. Pat. No. 5,340,564 and H. William Bosch et al., U.S. Pat. No. 5,510,118) emphasizing the usefulness of the drug delivery approach utilizing particulate aqueous suspensions.

In U.S. Pat. No. 5,246,707 Haynes teaches uses of phospholipid-coated microcrystals in the delivery of water-soluble biomolecules such as polypeptides and proteins. The proteins are rendered insoluble by complexation and the resulting material forms the solid core of the phospholipid-coated particle.

These patents and others utilized processes based on the particle size reduction by mechanical means such as attrition, cavitation, high-shear, impaction, etc achieved by media milling, high pressure homogenization, ultrasonication, and microfluidization of aqueous suspensions. However, these particle size reduction methods suffer from certain disadvantage, such as long process duration (high-pressure homogenization or microfluidization) and contamination (media milling, and ultrasonication). In addition, these methods may not be suitable for aqueous suspensions of compounds with limited stability in aqueous medium at the pH, high temperature and high pressure conditions prevailing in these processes.

Among the alternatives that address to these problems is a procedure which uses liquefied gasses for the production of microparticulate preparations. In one such method liquefied-gas solutions are sprayed to form aerosols from which fine solid particles precipitate. The phenomenon of solids precipitated from supercritical fluids was observed and documented as early as 1879 by Hannay, J. B. and Hogarth, J. "On the Solubility of Solids in Gases," Proc. Roy. Soc. London 1879 A29, 324, The first comprehensive study of rapid expansion from a liquefied-gas solution in the supercritical region was reported by Krukonis (1984) who formed micro-particles of an array of organic, inorganic, and biological materials. Most particle sizes reported for organic materials, such as lovastatin, polyhydroxyacids, and mevinolin, were in the 5–100 micron range. Nanoparticles of beta-carotene (300 nm) were formed by expansion of ethane into a viscous gelatin solution in order to inhibit post expansion particle aggregation. Mohamed, R. S., et al. (1988), "Solids Formation After the Expansion of Supercritical Mixtures," in Supercritical Fluid Science and Technology, Johnston, K. P. and Penninger, J. M. L., eds., describes the solution of the solids naphthalene and lovastatin in supercritical carbon dioxide and sudden reduction of pressure to achieve fine particles of the solute. The sudden reduction in pressure reduces the solvent power of the supercritical fluid, causing precipitation of the solute as fine particles.

Tom, J. W. and Debenedetti, P. B. (1991), "Particle Formation with Supercritical Fluids—a Review," J. Aerosol. Sci. 22:555–584, discusses rapid expansion of supercritical solutions techniques and their applications to inorganic, organic, pharmaceutical and polymeric materials. This technique is useful to comminute shock-sensitive solids, to produce intimate mixtures of amorphous materials, to form polymeric microspheres and deposit thin films.

Most studies of rapid expansion from supercritical solution on organic materials utilize supercritical carbon dioxide. However, ethane was preferred to carbon dioxide for beta-carotene because of certain chemical interactions. Carbon dioxide is generally preferred, alone or in combination with a cosolvent. Minute additions of a cosolvent can significantly influence the solvent properties. When cosolvents are used in rapid expansion from a supercritical solution, care is required to prevent de-solution of the particles due to solvent condensing in the nozzle. Normally, this is achieved by heating the supercritical fluid, prior to expansion, to a point where no condensate (mist) is visible at the nozzle tip.

A similar problem occurs when carbon dioxide is used. During adiabatic expansion (cooling), carbon dioxide will be in two phases unless sufficient heat is provided at the nozzle to maintain a gaseous state. Most investigators recognize this phenomenon and increase the pre-expansion temperature to prevent condensation and freezing in the nozzle. A significant heat input is required (40–50 kcal/kg)

to maintain carbon dioxide in the gaseous state. If this energy is supplied by increasing the pre-expansion temperature the density drops and consequently reduces the supercritical fluid's solvating power. This can lead to premature precipitation and clogging of the nozzle.

The solvent properties of liquefied-gas are strongly affected by their fluid density in the vicinity of the fluid's critical point. In rapid expansion from liquefied-gas solutions, a non-volatile solute is dissolved in a liquefied-gas that remains either in the supercritical or sub-critical phase. Nucleation and crystallization are triggered by reducing the solution density through rapid expansion of the liquefied-gas to atmospheric conditions. To achieve this the liquefied-gas is typically sprayed through 10–50 micron (internal diameter) nozzles with aspect ratios (L/D) of 5–100. High levels of supersaturation result in rapid nucleation rates and limited crystal growth. The combination of a rapidly propagating mechanical perturbation and high supersaturation is a distinguishing feature of rapid expansion from a liquefied-gas solution. These conditions lead to the formation of very small particles with a narrow particle size distribution.

There are a number of advantages in utilizing compressed carbon dioxide in the liquid and supercritical fluid states, as a solvent or anti-solvent for the formation of materials with submicron particle features. Diffusion coefficients of organic solvents in supercritical fluid carbon dioxide are typically 1–2 orders of magnitude higher than in conventional liquid solvents. Furthermore, carbon dioxide is a small linear molecule that diffuses more rapidly in liquids than do other antisolvents. In the antisolvent precipitation process, the accelerated mass transfer in both directions can facilitate very rapid phase separation and hence the production of materials with sub-micron features. It is easy to recycle the supercritical fluid solvent at the end of the process by simply reducing pressure. Since supercritical fluids do not have a surface tension, they can be removed without collapse of structure due to capillary forces. Solvent removal from the product is unusually rapid. No carbon dioxide residue is left in the product, and carbon dioxide has a number of other desirable characteristics, for example it is non-toxic, nonflammable, and inexpensive. Furthermore, solvent waste is greatly reduced since a typical ratio of antisolvent to solvent is 30:1.

Exploiting these concepts Henriksen et al. in WO 97/14407, disclosed a process using compressed fluids to produce sub-micron sized particles of water insoluble compounds with biological uses, particularly water insoluble drugs by precipitating a compound by rapid expansion from a supercritical solution in which the compound is dissolved, or precipitating a compound by spraying a solution, in which the compound is soluble, into compressed gas, liquid or supercritical fluid which is miscible with the solution but is antisolvent for the compound. In this manner precipitation with a compressed fluid antisolvent (compressed fluid antisolvent) is achieved.

An essential element of this process is the use of phospholipids and other surface modifiers to alter the surface of the drug particles to prevent particle aggregation and thereby improve both their storage stability and pharmacokinetic properties. This process combines or integrates phospholipids or other suitable surface modifiers such as surfactants, as the aqueous solution or dispersion in which the supercritical solution is sprayed. The surfactant is chosen to be active at the compound-water interface, but is not chosen to be active at the carbon dioxide-organic solvent or carbon dioxide-compound interface when carbon dioxide is used as the supercritical solution. The use of surface modifying agents in the aqueous medium allowed making submicron particles by the compressed fluid antisolvent process without particle aggregation or flocculation.

BRIEF DESCRIPTION OF THE DRAWINGS

FIG. 1 is a graph showing the size distribution (relative volume v. particle size in nm) of cyclosporine produced in Example 3, and FIG. 2 is a graph showing the size distribution (relative volume v. particle size in nm) of cyclosporine produced in Example 4, and

BRIEF DESCRIPTION OF THE INVENTION

However, this prior process suffered from a very long duration of spray of the supercritical solution to obtain a substantial quantity of the desired product. The long duration of spray-process may be attributed to a slow rate of association of the surface modifier molecules or their assemblies in the aqueous medium with the newly precipitated solute particles.

During experimentation with the process of WO 97/14407 described above it was surprisingly found that incorporation of a surface modifier in both the supercritical (or sub-critical) liquefied gas along with incorporation of a surface modifier in the water insoluble substance allowed one to achieve a very rapid production of surface stabilized nanometer- to micrometer-sized particulate suspensions. The principle feature of the present invention is believed to be rapid attainment of intimate contact of the dissolved drug and the surface modifier during the very fast precipitation step of the drug from their solution in the liquefied gas.

While very rapid precipitation is a characteristic of precipitation of solutes from liquefied gases, the rapid intimate contact with the surface modifier is achieved by having the surface modifiers dissolved in the liquefied-gas containing the dissolved drug. A rapid intimate contact between the surface modifier and the newly formed particle substantially inhibits the crystal growth of the newly formed particle. In addition, if the surface modifier(s) is not included with the dissolved drug the rate at which the liquefied-gas droplet containing the drug is brought into contact with the antisolvent is much slower if very small stable particles are to be obtained. Thus a key feature of the invention is the high productivity of the process.

Although at least one (first) surface modifier should be dissolved along with the water insoluble substance to be reduced in size in the liquefied gas in the inventive process, additional (second) surface modifying agents of the same or different chemical nature may also be included in the aqueous medium. Further, during or after precipitation the fluid streams may be subjected to additional high shear forces, cavitation or turbulence by a high-pressure homogenizer to facilitate intimate contact of the particle surface and the surface modifier. Thus, in those cases where all the surface modifier is dispersed in the aqueous medium and the liquefied gas contains only the water insoluble substance, additional high shear forces, cavitation or turbulence by a high-pressure homogenizer can be exploited to facilitate the intimate contact of the particle surface and the surface modifier.

Thus, the overall objective of the present invention is to develop a process with high productivity based on the use of liquefied gas solvents, including supercritical fluid technology, that yields surface modifier stabilized suspensions of water insoluble drugs with an average particle size of 50 nm to about 2000 nm and a narrow size distribution. The process is robust, scalable and applicable to a wide range of water-insoluble compounds with biological uses.

DETAILED DESCRIPTION OF THE INVENTION

The present invention includes procedures for using super critical or compressed fluids to form surface modified particles of up to about 2000 nm in size and usually below 1000 nm, desirably less than 500 nm, preferably less than about 200 nm and often in a range of 5 to 100 nm in size. The size of the particles refers to volume weighted mean diameters of these particles suspended in aqueous medium.

The process of the present invention includes forming aqueous microparticulate suspensions of water insoluble or poorly water soluble compounds while simultaneously stabilizing of same with surface modifier molecules by rapid expansion into an aqueous medium from a compressed solution of the compound and surface modifiers in a liquefied-gas (Rapid Expansion of Liquefied Gas Solution, RELGS).

Alternatively another embodiment of the invention includes forming aqueous microparticulate suspensions of water insoluble or poorly water soluble compounds while simultaneously stabilizing the same with surface modifier molecules by rapid expansion into an aqueous medium of a compressed solution of the compound and surface modifiers in a liquefied-gas and homogenizing the aqueous suspension thus formed with a high pressure homogenizer (Rapid Expansion of Liquefied-Gas Solution and Homogenization, RELGS-H).

While not wishing to be bound by any particular theory, the processes of this invention are believed to induce rapid nucleation of the liquefied-gas dissolved drugs and other biologically active substances in the presence of surface modifying agents resulting in particle formation with a desirable size distribution in a very short time. Phospholipids or other suitable surface modifiers such as surfactants, as may be required, may be integrated into the processes as a solution or dispersion in the liquefied gas. In addition, the surface modifier may or may not be incorporated via its solution or dispersion in the aqueous medium. Alternatively, some of the surface modifiers may be dissolved in the liquefied gas along with the water insoluble substance and expanded into a homogenized aqueous dispersion of rest of the surface modifier of the formulation. The introduction of suitable surface modifying agents in the above noted processes serves to stabilize the generated small particles and suppress any tendency of particle agglomeration or particle growth while they are formed.

By industrially useful insoluble or poorly soluble compounds we include biologically useful compounds, imaging agents, pharmaceutically useful compounds and in particular drugs for human and veterinary medicine. Usually, the water insoluble compounds are those having a poor solubility in water, that is less than 5 mg/mL at a physiological pH of 6.5 to 7.4, although the water solubility may be less than 1 mg/mL and even less than 0.1 mg/mL.

Examples of some preferred water-insoluble drugs include immunosuppressive and immunoactive agents, antiviral and antifungal agents, antineoplastic agents, analgesic and anti-inflammatory agents, antibiotics, anti-epileptics, anesthetics, hypnotics, sedatives, antipsychotic agents, neuroleptic agents, antidepressants, anxiolytics, anticonvulsant agents, antagonists, neuron blocking agents, anticholinergic and cholinomimetic agents, antimuscarinic and muscarinic agents, antiadrenergic and antiarrhythmics, antihypertensive agents, antineoplastic agents, hormones, and nutrients. A detailed description of these and other suitable drugs may be found in Remington's Pharmaceutical Sciences, 18th edition, 1990, Mack Publishing Co. Philadelphia, Pa.

A range of compressed gases in the supercritical or sub-critical fluid phases have been reported in the prior art (for example, U.S. Pat. No. 5,776,486, and Tom, J. W. and Debenedetti, P. B. (1991), "Particle Formation with Supercritical Fluids—a Review," J. Aerosol. Sci. 22:555–584) from which a suitable gas may be selected for the purpose of the present invention. These include but are not limited to gaseous oxides such as carbon dioxide and nitrous oxide; alkanes such as ethane, propane, butane, and pentane; alkenes such as ethylene and propylene; alcohols such as ethanol and isopropanol; ketones such as acetone; ethers such as dimethyl or diethyl ether; esters such as ethyl acetate; halogenated compounds including sulfur hexafluoride, chlorofluorocarbons such as trichlorofluoromethane ($CCl_3F$, also known as Freon 11), dichlorofluoromethane ($CHCl_2F$, also known as Freon 21), difluorochloromethane ($CHClF_2$, also known as Freon 22), and fluorocarbons such as trifluoromethane ($CHF_3$, also known as Freon 23); and elemental liquefied gases such as xenon and nitrogen and other liquefied compressed gases known to the art.

Liquefied carbon dioxide was used to prepare rapid expansion solutions of the drugs described in the following examples. Carbon dioxide has a critical temperature of 31.3 degrees C. and a critical pressure of 72.9 atmospheres (1072 psi), low chemical reactivity, physiological safety, and relatively low cost. Another preferred supercritical fluid is propane.

Examples of some suitable surface modifiers include: (a) natural surfactants, such as casein, gelatin, natural phospholipids, tragacanth, waxes, enteric resins, paraffin, acacia, gelatin, and cholesterol, (b) nonionic surfactants such as polyoxyethylene fatty alcohol ethers, sorbitan fatty acid esters, polyoxyethylene fatty acid esters, sorbitan esters, glycerol monostearate, polyethylene glycols, cetyl alcohol, cetostearyl alcohol, stearyl alcohol, poloxamers, polaxamines, methylcellulose, hydroxycellulose, hydroxy propylcellulose, hydroxy propylmethylcellulose, noncrystalline cellulose, and synthetic phospholipids, (c) anionic surfactants such as potassium laurate, triethanolamine stearate, sodium lauryl sulfate, alkyl polyoxyethylene sulfates, sodium alginate, dioctyl sodium sulfosuccinate, negatively charged phospholipids (phosphatidyl glycerol, phosphatidyl inosite, phosphatidylserine, phosphatidic acid and their salts), and negatively charged glyceryl esters, sodium carboxymethylcellulose, and calcium carboxymethylcellulose, (d) cationic surfactants such as quaternary ammonium compounds, benzalkonium chloride, cetyltrimethylammonium bromide, and lauryldimethylbenzyl-ammonium chloride, (e) colloidal clays such as bentonite and veegum, (f) natural or synthetic phospholipid, for example phosphatidylcholine, phosphatidylethanolamine, phosphatidylserine, phosphatidylinositol, phosphatidylglycerol, phosphatidic acid, lysophospholipids, egg or soybean phospholipid or a combination thereof. The phospholipid may be salted or desalted, hydrogenated or partially hydrogenated or natural semisynthetic or synthetic. A detailed description of these surfactants may be found in Remington's Pharmaceutical Sciences, 18th Edition, 1990, Mack Publishing Co., PA; and Theory and Practice of Industrial Pharmacy, Lachman et al., 1986.

The following examples further explain and illustrate the invention:

EXAMPLE 1
Phase Behavior of Water Insoluble Compound in Compressed Liquefied Gasses.

In order to assess whether a particular water insoluble compound should be formulated as an aqueous submicron particulate suspension from its solution in the liquefied gasses, the solubility of the candidate drugs in the liquefied gasses was measured.

To prepare solutions with a constant molar composition, measured amounts of drug (fenofibrate) were charged to a constant volume view cell. Temperature was kept constant at 60° C. Pressure was varied from 1300 to 4000 psi by pumping the compressed liquefied gas into the view cell. The phase behavior was determined visually by noting the pressure at which the solid drug appeared to dissolve. A summary of fenofibrate solubility in liquefied carbon dioxide, propane and ethane is given in Table I. The solubility values of >1% w/w in any solvent would allow the fine-particulate preparation from these solvents.

TABLE I

Fenofibrate Solubility Experiment in Liquefied Carbon Dioxide, Propane and Ethane at 60° C.

| Liquefied gas | Pressure (psi) | Solubility (%, w/w) |
| --- | --- | --- |
| Carbon Dioxide | 1800 | 0.01 |
|  | 2000 | 0.08 |
|  | 2800 | 1.4 |
| Propane | 1500 | 2.5 |
|  | 2000 | 2.3 |
| Ethane | 1300 | 0.016 |
|  | 2000 | 0.79 |
|  | 3000 | 1.80 |
|  | 4000 | 1.90 |

EXAMPLE 2
Fenofibrate Microparticle Formation by the RELGS Process

A solution containing Fenofibrate (2 g), Lipoid E-80 (0.2 g), Tween-80 (0.2 g) in the liquefied carbon dioxide pressurized to 3000 psi was expanded through a 50 mm orifice plate into water held at atmospheric pressure and room temperature (22° C.). A fine suspension of fenofibrate was obtained with a mean particle size of about 200 nm. The particle sizing was performed by photon correlation spectroscopy using Submicron Particle Sizer-Autodilute Model 370 (NICOMP Particle Sizing Systems, Santa Barbara, Calif.). This instrument provides number weighted, intensity weighted, and volume weighted particle size distributions as well as multi-modality of the particle size distribution, if present.

EXAMPLE 3

A fine spray-nozzle was constructed with PEEK capillary tubing of an internal diameter of 63.5 mm. This PEEK nozzle was fastened with a M-100 Minitight male nut and attached to an Upchurch SS20V union body which was further attached to a ¼ inch high pressure manifold via Swagelok™ brand fittings of appropriate size. Except for the PEEK tubing all other components were made up of 316 stainless steel. A liquefied gas solution of the water insoluble substance was introduced at high pressure (>1000 psig) through the ¼ inch high pressure manifold into the 63.5 mm PEEK nozzle to be expanded into the aqueous medium. The vessel for the liquefied gas solution was charged with 1 g of cyclosporine and 0.2 g of Tween-80. The vessel was filled with carbon dioxide at 5000 psig and heated to about 24° C. The vessel was allowed to stand for about 20 minutes for complete dissolution and for attaining equilibrium. Separately, a 2% w/w suspension of egg phospholipid (Lipoid E80 from Lipoid GmbH) in a 5.5% solution of mannitol was homogenized at 6000 psi with an Avestin Emulsiflex C50 homogenizer (Avestin Inc, Ottawa, Canada) for 15 min when it produced a clear dispersion. The pH of the phospholipid suspension was adjusted to 8.0 with aqueous NaOH solution prior to homogenization. The carbon dioxide solution of cyclosporine and Tween-80 that was held at 24° C. and 5000 psig was expanded into the aqueous dispersion of egg phospholipid. Very rapidly, in about 3 minutes, a translucent aqueous suspension of about 23 nanometer particle size was obtained (See FIG. 1). This example provides a simple scalable process by the way of incorporation of several such PEEK nozzles within a manifold and simultaneously expanding into a reservoir containing appropriate amount of the aqueous medium. The PEEK nozzle is known to be inert and very inexpensive. Construction of the nozzle is very simple and can be done in less than 10 minutes.

EXAMPLE 4

Cyclosporine Microparticle Formation by the RELGS-H Process

An aqueous suspension containing Mannitol (5.5%), Lipoid E-80 (2%), and Tween 80 (2%), was prepared. A solution of cyclosporine in the Liquifed gas was also prepared and kept at 2000 psig and 60° C. This solution was expanded through a 63.5 mm PEEK nozzle into the aqueous suspension. A suspension of about 3 g cyclosporine was made in this way. The resulting suspension was homogenized for 8 passes at 6,000 psig. The final mean particle size after homogenization was 86 nanometers with the 99 percentile at 150 nm (see FIG. 2) as measured using the Submicron Particle Sizer-Autodilute Model 370 (NICOMP Particle Sizing Systems, Santa Barbara, Calif.).

While the invention has been described in connection with what is presently considered to be the most practical and preferred embodiment, it is to be understood that the invention is not to be limited to the disclosed embodiment, but on the contrary, is intended to cover various modifications and equivalent arrangements included within the spirit and scope of the appended claims.

What is claimed is:

1. A process of preparing a stable suspension of submicron particles of a water-insoluble or substantially water-insoluble biologically active compound of up to 2000 nm in size comprising the successive steps of:

(a) dissolving a water-insoluble or substantially water-insoluble biologically active compound and a first surface modifier in a liquefied compressed gas solvent therefor and forming a solution of greater than 1% w/w of said compound in said solvent and thereafter;

(b) expanding the compressed fluid solution prepared in step (a) into water or aqueous solution containing a second surface modifier and water-soluble agents thereby producing a suspension of microparticles, and thereafter (c) homogenizing the suspension of step (b) at high pressure.

2. The process according to claim 1, including the additional step of (d) recovering the microparticles so produced.

3. The process according to claim 1, wherein the first surface modifier and the second surface modifier are the same.

4. The process according to claim 1, wherein the first surface modifier and the second surface modifier are different.

5. The process according to claim 1, wherein one or both of the surface modifiers is a phospholipid.

6. The process according to claim 1, wherein one or both the surface modifiers is a surfactant.

7. The process of claim 1 wherein one or both of the surface modifiers is a mixture of two or more surfactants.

8. The process according to claim 1, wherein at least one surface modifier is a surfactant devoid or substantially completely devoid of phospholipid.

9. The process of claim 6 wherein the surface modifier is a polyoxyethylene sorbitan fatty acid ester, a block copolymer of ethylene oxide and propylene oxide, a tetrafunctional block copolymer derived from sequential addition of ethylene oxide and propylene oxide to ethylenediamine, an alkyl aryl polyether sulfonate, polyethylene glycol, hydroxy propylmethylcellulose, sodium dodecylsulfate, sodium deoxycholate, cetyltrimethylammonium bromide or combinations thereof.

10. The process of claim 5 wherein the surface modifier is of egg or plant phospholipid or semisynthetic or synthetic in partly or fully hydrogenated or in a desalted or salt phospholipid such as phosphatidylcholine, phospholipon 90 H or dimyristoyl phosphatidylglyerol sodium salt, phosphatidylethanolamine, phosphatidylserine, phosphatidic acid, lysophospholipids or combinations thereof.

11. The process of claim 1 wherein the compound is a cyclosporine, fenofibrate, or alphaxalone.

12. The process of claim 1 wherein the particles produced are less than 500 nm in size.

13. The process of claim 12 wherein the particles produced range from 5 up to about 200 nm in size.

14. The process of claim 1 wherein 99% of the particles produced are below 2000 nm.

15. The process of claim 1 wherein the liquefied compressed gas is carbon dioxide in the supercritical or subcritical phase.

* * * * *